United States Patent [19]

Thieme et al.

[11] Patent Number: 5,714,341
[45] Date of Patent: Feb. 3, 1998

[54] SALIVA ASSAY METHOD AND DEVICE

[75] Inventors: Thomas R. Thieme, Independence; B. Melina Cimler, Portland; Nanette M. Klimkow, Beaverton, all of Oreg.

[73] Assignee: Epitope, Inc., Beaverton, Oreg.

[21] Appl. No.: 219,977

[22] Filed: Mar. 30, 1994

[51] Int. Cl.$^6$ .................. C12Q 1/40; G01N 21/00; A61B 5/00
[52] U.S. Cl. .................. 435/22; 435/4; 435/29; 435/805; 435/810; 436/63; 422/56; 422/58; 422/61; 422/102; 128/760; 128/762; 128/769; 128/771
[58] Field of Search .................. 435/22, 4, 29, 435/805, 810; 436/63; 422/56, 58, 61, 102; 128/760, 762, 769, 771

[56] References Cited

U.S. PATENT DOCUMENTS

| | | | |
|---|---|---|---|
| 2,850,903 | 9/1958 | Schwerin | 435/22 |
| 4,582,795 | 4/1986 | Shibuya et al. | 435/34 |
| 4,853,325 | 8/1989 | Vodian et al. | 435/5 |
| 5,036,000 | 7/1991 | Palmer et al. | 435/26 |
| 5,056,521 | 10/1991 | Parsons et al. | 128/635 |
| 5,103,836 | 4/1992 | Goldstein et al. | 128/760 |
| 5,149,623 | 9/1992 | Carlson et al. | 435/5 |
| 5,334,502 | 8/1994 | Sangha | 435/7.21 |
| 5,339,829 | 8/1994 | Thieme et al. | 128/760 |
| 5,479,937 | 1/1996 | Thieme et al. | 128/760 |

FOREIGN PATENT DOCUMENTS

| | | |
|---|---|---|
| 0 083 941 | 7/1983 | European Pat. Off. . |
| 520408A2 | 12/1992 | European Pat. Off. . |
| WO 91/14944 | 10/1991 | WIPO . |
| WO93/11434 | 6/1993 | WIPO . |

OTHER PUBLICATIONS

Thieme et al, *J. Clin. Microbiol.*, vol. 30, No. 5, pp. 1076–1079, May 1992.

Winn–Deen et al, *Clin. Chem.*, vol. 34, No. 10, pp. 2005–2008, 1988.

Wallenfels et al, *Chemical Abstracts*, vol. 100, p. 206, Ref. #81626s, 1984 (Aerzl. Lab. 1983, 29(11), 339–48).

*Primary Examiner*—Cecilia J. Tsang
*Assistant Examiner*—Abdel A. Mohamed
*Attorney, Agent, or Firm*—Townsend and Townsend and Crew LLP

[57] ABSTRACT

An improved method for determining the presence of an analyte in an oral fluid sample. A portion of the sample is mixed or contacted with a chromogenic substrate effective to produce a colored product upon reaction with α-amylase present in the sample. After a selected reaction time, the reaction mixture is inspected to determine the level of such colored product produced. Production of a level of colored product above a selected threshold within the reaction time indicates that an effective volume of undiluted oral fluid sample has been collected which is sufficient to allow detection of the analyte. A device for use in the method is also disclosed.

20 Claims, 2 Drawing Sheets

SALIVA ASSAY METHOD AND DEVICE

FIELD OF THE INVENTION

The present invention relates to methods of analyzing saliva for the presence of selected analytes.

REFERENCES

Parry, J. V., et al., Lancet 2:72–75 (1987).

Thieme, T., et al., J. Clin. Microbiol. 20:1076–1079 (1992a).

Thieme, T., et al., "Oral Fluid Sampling for Determination of HIV-I Antibody Serostatus," Abstract from VIII Int'l. Conf. on AIDS, pg. C328 (1992b).

BACKGROUND OF THE INVENTION

A number of analytical procedures and devices are commonly used to test body fluids for the presence of substances of diagnostic value. Most procedures today are based on analysis of blood or urine. An advantage of blood as a test fluid is that analytes are often present at relatively high concentrations, and measurements of these concentrations can often provide information about a patient's health. Urine is useful for diagnostic testing when the blood component of interest (e.g., a low molecular weight drug or hormone) is concentrated during urine formation. However, the urine concentration of an analyte does not usually reflect the physiologically active amount of the analyte in blood.

Although saliva has not been commonly used as a body fluid in medical diagnosis, numerous studies (Parry et al., 1987; Thieme et al., 1992 a, b) have demonstrated that oral fluids may be used for diagnostic testing for antibodies or antigens specific for various human or animal pathogens. Oral fluids have also been shown to be useful in measuring the body levels of therapeutic drugs, drugs of abuse, and naturally occurring hormones.

Devices for collection of oral fluid have been described. U.S. Pat. Nos. 4,418,702 and 4,580,577 show an absorbent pad for collecting oral fluid, and a barrel-piston arrangement for extracting the fluid from the pad.

U.S. Pat. No. 4,774,962 describes an absorbent pad for collecting saliva, and a centrifuge tube and tube-insert for removing oral fluid from the pad by centrifugation.

U.S. Pat. No. 5,056,521 describes an apparatus for includes a barrel-piston arrangement having a nonreactive absorbent swab secured to the piston. The barrel and piston are used to squeeze the fluid sample from the swab into a glucose monitoring instrument.

PCT Publication No. WO 91/13355 and U.S. Pat. No. 5,103,836 disclose a method and device for collecting analytes from the oral cavity for testing. The method employs an absorbent pad impregnated with the salts of a hypertonic solution effective to recover a high concentration of the analyte.

EPO Publication No. 520408 A2 and U.S. Pat. No. 5,260,031 describe sampling devices for collecting biological fluids such as saliva. The '031 patent describes a device that includes a piece of filter paper fixed to a holder for collecting a saliva sample, and an indicator for determining that a selected volume of sample has been collected.

One difficulty in the testing of saliva is that the saliva sample may be relatively dilute, because of a recent intake of liquids, for example. Where the sample is to be tested for an analyte whose presence indicates a specific disease state, a dilute saliva sample can give rise to a negative test result because the analyte is too dilute to be detected.

A further problem with saliva is that unlike blood, which can be easily recognized by virtue of its color, saliva is colorless and may therefore be indistinguishable in appearance from water. In situations where an insurance representative must collect a saliva sample from a test subject, the subject may be able to evade the test by providing a water sample rather than a saliva sample.

Since false negatives can seriously undermine the reliability of analyte testing in saliva, it would be desirable to have a method that provides rapid assessment of the dilution state of a collected saliva sample. Such a method could significantly enhance the reliability of saliva-based diagnostic tests, by establishing whether a collected sample is a saliva sample that is sufficiently concentrated to allow reliable detection of the analyte of interest.

SUMMARY OF THE INVENTION

The present invention relates to an improvement for methods of determining the presence of an analyte in a saliva sample, where a variable volume of sample is collected from the mouth of a human subject for testing in an analyte assay.

In the method of the invention, a portion of the sample is contacted with a chromogenic substrate effective to produce a colored product upon reaction with α-amylase present in the sample. After a selected reaction time, the reaction mixture is inspected to determine the level of colored product produced within the selected time. Production of a level of colored product above a selected threshold level indicates that an effective volume of undiluted saliva has been collected that is sufficient to allow detection of the analyte in the analyte assay.

In one embodiment, the chromogenic substrate is localized on a collection device which includes (i) an absorbent pad for collecting oral fluid when the pad is placed in a subject's mouth, and (ii) a reaction region containing the substrate, which is located downstream from the pad on the device for absorbing oral fluid from the pad after oral fluid has been absorbed by the pad. The device may additionally include a detection region downstream from the reaction region for timing purposes, such that the reaction region is inspected after the fluid reaches the detection region.

In another embodiment, the sample is collected in an absorbent pad which is then submerged in a vessel having a known volume of reaction medium containing the amylase substrate.

The method is useful in assays for detecting a variety of analytes including immunoglobulins, viral and other microbial antigens, hormones and hormone derivatives, and drugs and drug metabolites. In one embodiment, the level of colored product produced in the reaction is used as an indicator of the level of total immunoglobulins in the sample.

In another aspect, the invention includes a device which can be used in accordance with the method described above. The device includes (i) an absorbent pad for collecting oral fluid when placed in a subject's mouth, and (ii) reagent means for producing a threshold level of a colored reaction product when oral fluid from the absorbent pad is contacted with the reagent means for a selected time period. An above-threshold level of colored reaction produced within the selected time period indicates that an effective volume of undiluted saliva sample sufficient to allow detection of the analyte in such assay has been collected.

In one embodiment, the reagent means includes a selected volume of a solution containing the chromogenic amylase substrate. Submersion of the adsorbent pad, after collection of oral fluid in the pad, in the solution for a selected time is effective to produce a threshold solution color when the pad contains an effective volume of undiluted saliva.

In another embodiment, the reagent means includes a chromogenic amylase substrate localized in a reaction region downstream from the absorbent pad, for receiving oral fluid collected in the pad. The device may further include a detection region downstream from the reaction region, for timing purposes. The reaction and detection regions are spaced apart such that migration of the oral fluid from the reaction region to the detection region occurs over the selected time period.

These and other objects and features of the invention will be more fully appreciated when the following detailed description of the invention is read in conjunction with the accompanying drawings.

DETAILED DESCRIPTION OF THE INVENTION

I. Definitions

Figure 1:
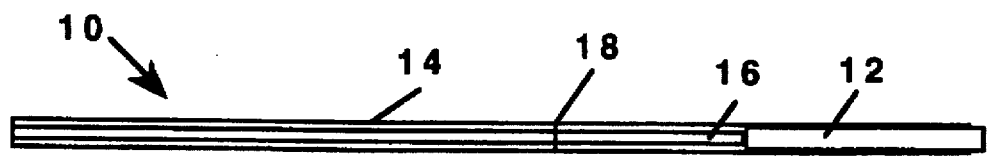
FIG. 1 shows a top plan view of a sample collection device 10 which can be used in accordance with the invention.

An "effective volume of undiluted saliva sample sufficient to allow detection of analyte" refers to a saliva sample that is sufficient in volume and concentration to allow reliable detection of an analyte of interest using an assay which has a known limit of detection for the analyte.

II. General Features of the Method of the Invention

The present invention addresses the problems of false saliva samples and saliva samples that are too dilute to allow reliable detection of an analyte of interest.

In the method of the invention, a saliva sample is collected from the oral cavity of the subject, typically by placing an absorbent material in the form of a pad or swab in the subject's mouth. The absorbent material may be any of a number of absorbent materials suitable for oral use. Suitable materials include but are not limited to the following: absorbent cotton, filter paper, such as commonly used in dental procedures, cellulose-based materials, polyurethane, polyester, and rayon.

The region of the mouth from which the sample is collected may depend on the particular analyte that is to be tested for. For example, according to U.S. Pat. No. 5,056,521, saliva for glucose measurements is preferably collected from the space between the upper gum and the upper lip. More typically, the sample can be collected from the area between the cheek and lower gums (lower buccal space), to facilitate absorption of secretions originating from the gingival and submucosal lymphoid tissues as well as from salivary glands.

To improve the recovery of analyte during sample collection, the absorbent material can be impregnated with the salts of a hypertonic solution, as taught in U.S. Pat. No. 5,103,836 which is incorporated herein by reference. With respect to salivary immunoglobulins, for example, it is possible to increase immunoglobulin recovery by as much as 8- to 16-fold. The absorbent material may also contain flavorants to promote salivation.

In addition to the use of absorbent materials such as above, the saliva sample can be collected by other methods, e.g., by aspiration.

In the next step in the method, at least a portion of the collected sample is mixed or contacted with a chromogenic substrate effective to produce a colored product upon reaction with amylase in the sample. After a selected reaction time, the reacted sample is inspected to determine the level of color produced in the reaction. A level of color above a selected threshold indicates that an effective volume of saliva has been collected.

The chromogenic substrate for use in the invention is any substrate which is specifically cleavable by salivary α-amylase (as opposed to other salivary components) to produce a colored product that is visible to the human eye.

Preferred amylase substrates and methods for preparing them are described in U.S. Pat. No. 4,963,479 entitled "Reagent System for an Alpha-Amylase Assay Containing Aromatic substituted Glycoside," which is incorporated herein by reference. These preferred substrates are characterized by a tri- or tetraglucoside structure in which the terminal glucosyl group contains an acetal moiety at C-1 with an aromatic R group attached to the acetal oxygen. The configuration of the acetal carbon is alpha.

These substrates are effective to release aryl alcohols which are colored in aqueous solution. Preferably, the aryl alcohols contain electron-withdrawing substituents effective to stabilize the deprotonated (aryloxy anion) form of the aryl alcohol. For example, where the aryl alcohol is p-nitrophenol, the nitro group is effective to stabilize the aryloxy anion form by electron-delocalization.

The aryl group may also include other electron-withdrawing groups to further stabilize the aryloxy anion form and produce a more intense color. In one preferred embodiment, the substrate is 2-chloro-4-nitrophenyl-α-D-maltotrioside, which releases 2-chloro-4-nitrophenol when catalytically cleaved by salivary α-amylase.

It will be appreciated that amylase substrates containing sugar groups differing from the above polyglucosides, e.g., having different stereochemical configurations and/or sugar substituents, may also be used.

The saliva sample and amylase substrate are caused to contact each other under reaction conditions effective to promote cleavage of the substrate by amylase present in the sample. Typically, an aqueous solution buffered in a pH range of about 4 to about 8 is appropriate. Buffers that may be used include phosphate, citrate, acetate, and MES (2-(N-morpholino)-ethanesulfonaic acid), for example. The reaction conditions may also include other reagents that accelerate the catalytic rate of salivary α-amylase, such as azide ($N_3^-$) or thiocyanate ($SCN^-$). For example, sodium azide at a concentration of 230 mM has been shown to increase the catalytic rate of salivary α-amylase by about 7-fold (U.S. Pat. No. 4,963,479). However, lower concentrations of such accelerants (e.g., 5 mM sodium thiocyanate) are also effective. The conditions may also include calcium ($Ca^{2+}$), a cofactor of α-amylase.

As the reaction proceeds, the reaction mixture changes color at a rate proportional to the amount of amylase in the sample. The reaction is allowed to proceed until the desired degree of color has appeared, or until a selected amount of time has passed following the start of the reaction.

Whether the desired level of color has been achieved can be determined by comparing the color in the reaction mixture with that of an appropriate standard, such as a color strip having a selected color intensity level. In one embodiment, the intensity of the color standard is selected to reflect a minimum threshold necessary to allow reliable detection of the analyte of interest in the sample. Color production that matches or exceeds the threshold level indicates that the sample will provide a reliable test result for the analyte of interest, and in particular, that a negative result will likely be a reliable result.

The method of the invention is useful for facilitating diagnosis of infection and other disease states in human subjects by detecting the presence of a disease-related analyte that is not ordinarily present or that is elevated above its normal level. The method also contemplates detection of disease states associated with reduced levels of substances that are secreted in the saliva of healthy subjects. She method may also find use for detecting drug abuse, or for verifying patient compliance in drug therapy. The method is compatible with a variety of oral fluid analytes. Such analytes include, but are not limited to, drugs or drug metabolites such as cocaine, benzoylegonine, cotinine, amphetamine, or methamphetamine; viral and bacterial antigens, such as antigens derived from hepatitis B, HIV-1 and HIV-2; immunoglobulins, such as particular immunoglobulin classes (e.g. IgG and IgM) or immunoglobulins specific against viral or bacterial pathogens, including immunoglobulins specific for hepatitis A, measles, rubella, mumps, and *Helicobacter pylori*; and hormones or hormone metabolites, such as β-hCG.

The selected color threshold and reaction time employed in the invention are tailored according to the expected concentration of the analyte of interest, and thus, to the α-amylase concentration that is suitable to indicate that an effective volume of undiluted sample has been collected.

To determine an α-amylase concentration which may be suitable as a threshold in testing for a particular analyte, oral fluid samples from healthy subjects (controls) and affected subjects (individuals having a condition associated with a significantly increased or decreased salivary level of a particular diagnostic analyte) are tested to establish analyte concentrations range that are characteristic of the control and affected subjects, respectively. The analyte concentrations may be measured by any method suitable for the analyte, e.g., by immunoassay or HPLC. Conveniently, the analyte may be measured using a commercial assay kit if available.

Typically, the analyte is one that is present in affected subjects but not in healthy subjects. Depending on the nature of the analyte, detection of the analyte may indicate, for example, that the subject has a particular disease condition, has an adequate vaccination status against a particular pathogen, is in compliance or non-compliance with a therapeutic regimen, or may have a drug abuse problem.

For detection of the analyte, the concentration range of the analyte when present in undiluted oral fluid should fall in a range whose lower limit is at least two standard deviations above the threshold analyte concentration that can be detected by the analyte assay. Preferably, the lower limit of the concentration range is at least ten times the detection limit of the analyte assay.

Since α-amylase may be readily detected in an undiluted saliva sample by the method of the invention, the threshold level of α-amylase used in assessing the relative concentration of the oral fluid may be tailored according to the detection limit of the analyte assay. If the analyte to be detected is ordinarily present at a high concentration, a relatively dilute saliva sample may still provide enough analyte to be detected in the analyte assay, so that a relatively low amylase threshold may be used. Conversely, if the analyte is ordinarily present at low concentrations, then a relatively high amylase threshold should be used since dilution of the sample (e.g., by the subject's drinking water just before sample collection) may render the analyte undetectable in the analyte assay.

Once a threshold α-amylase concentration has been selected for the particular analyte to be assayed, the reaction reagents used to measure the α-amylase may be adapted so that reaction of the amylase substrate with the threshold level of amylase will produce colored product within a time period that is convenient to the user. For example, the assay conditions detailed in Example 1 are effective to produce a result as to the concentration sufficiency of oral fluid samples within about two or three minutes.

In another embodiment, the color of the reaction mixture can be compared with a set of color strips having a range of intensities. The color intensity produced in the reaction mixture after a selected time is matched with the standard strip having the closest intensity, and the closest match is recorded. Since a greater color intensity reflects a greater concentration of salivary components in the sample, the strips can be used to establish a confidence level for the result (probability of reliable analyte detection). In other words, the greater the color intensity, the greater the probability that the saliva sample is adequately concentrated for reliable detection of the analyte. The confidence level associated with a given color intensity can be determined by statistical analysis of diluted saliva samples containing appropriate ranges of analyte concentrations.

III. α-Amylase Substrate Solution

In one aspect, the method of the invention can be carried out by collecting the sample from the subject's mouth using an absorbent pad or the like. After the pad has been imbued with saliva (usually after about 2 minutes), the pad is submerged in a vessel having a known volume of reaction medium that contains the chromogenic amylase substrate. The reaction is allowed to proceed until a threshold level of color has been produced or until a selected time has passed, as set forth above. The result of the reaction is then used to determine whether a sufficiently concentrated sample has been collected.

Since most analyte assays require a minimum sample volume, the absorbent material should be sized so as to ensure collection of at least that amount, by suitable choice of size dimensions. Conveniently, the amount of saliva to be absorbed in the pad can be between 0.1 and 0.5 mL, although other volumes outside of this range may be satisfactory.

Figure 2:
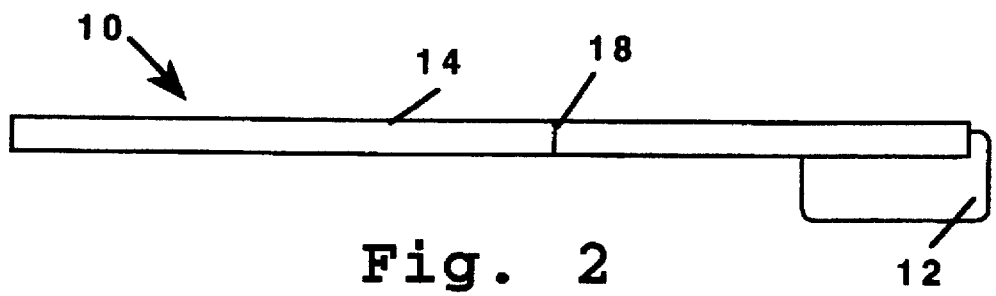
FIG. 2 shows a side view of the device shown in FIG. 1.

FIGS. 1 and 2 show a top plan view and side view of a sample collection device 10 which may be used in accordance with the invention. The device includes a pad 12 and a handle 14 which contains a groove 16 for holding the pad. The device also includes a score mark 18 which allows handle 14 to be broken off easily. The handle is used to place the pad in the subject's mouth to collect a saliva sample.

Figure 3A:
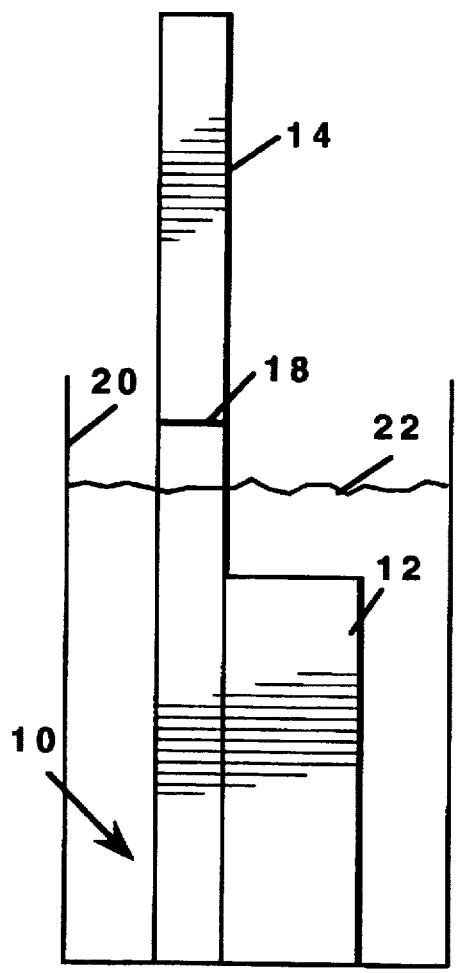
FIGS. 3A and 3B illustrates use of the FIG. 1 device for delivering a saliva sample to a storage solution in accordance with the invention.

After sample has been collected in the pad, the pad is removed from the subject's mouth and placed in a vial containing a selected volume of α-amylase substrate solution. FIG. 3A shows device 10 in a vial 20 such that pad 12 is submerged in substrate solution 22.

Besides an α-amylase substrate, solution 20 may also comprise buffer reagents to maintain a pH preferably between 4 and 8, a salt or salts to adjust ionic strength, an optional accelerant such as hydrazide or thiocyanate to increase the catalytic rate of the amylase, and calcium ions as an amylase cofactor. The substrate solution may also include a preservative such as an anti-bacterial agent, an anti-fungal agent, or enzyme inhibitors. Examples of preservatives include but are not limited to benzoic acid, sorbic acid, thimerosal, sodium azide, chlorhexidine gluconate, and benzalkonium chloride. It is preferred to use such preservatives in a range of about 0.01% to about 0.2% by weight.

Upon contact of the pad with the solution, the amylase substrate diffuses into the pad and is converted to colored product by amylase present in the sample. The development of color in the pad is then monitored as above. Although the vial can be shaken, or the pad squeezed, to facilitate reaction of the substrate with amylase, leaving the solution undisturbed during the reaction may be sufficient.

Figure 3B:
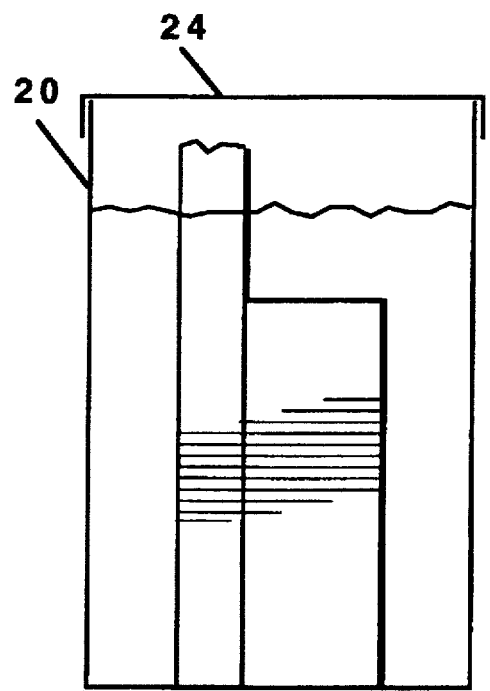

After the desired color level has been produce, or a selected time has passed, the handle may be broken off at score mark 18 and the vial sealed with to cover 24 (FIG. 3B). The sample is then ready for transport to a diagnostic lab to test for analyte.

Example 1 describes a study in which saliva samples from 73 healthy adults were used to demonstrate an exemplary embodiment of the invention. The saliva samples were collected in absorbent pads using a device of the type shown in FIGS. 1 and 2 and then transferred to transparent vials loaded with a reaction solution (0.8 ml) containing the substrate 2-chloro-4-nitrophenyl-α-D-maltotrioside at a concentration of 0.76 mM. Upon cleavage by α-amylase, this substrate produces a yellow-colored solution due to the phenolic product that is released (2-chloro-4-nitrophenol).

The submerged pads were monitored for several minutes following contact with the substrate solutions to determine when certain intensity levels were achieved, as judged by comparison with three color swatches of increasing intensity (Int 1, Int 2, and Int 3). The results are shown in Table 1 below.

TABLE 1

| | TIME TO ACHIEVE INTENSITY LEVEL (SEC) | | |
|---|---|---|---|
| | Int 1 | Int 2 | Int 3 |
| Avg | 19 | 49 | 130 |
| SD | 6.5 | 21 | 58 |

As can be seen from Table 1, the samples were effective to cleave the amylase substrate to produce colored product at approximately the same rates. The results are consistent with the α-amylase concentrations falling within a defined concentration range.

Further studies conducted in support of the invention indicate that the method of the invention is useful for tests for assessing HIV-1 status (i.e., detecting anti-HIV-1 antibodies), and in assessing the immunization status of subjects with respect to measles, mumps, and rubella. In this respect, the applicants have found that samples containing a total IgG concentration of greater than about 1 µg/ml are suitable for reliable detection of antibodies specific for HIV-1, measles, mumps, and rubella, so that an α-amylase threshold chosen to indicate whether a normal concentration of total salivary immunoglobulins is present can be used as a preliminary screen as to whether the sample is sufficiently concentrated for further testing.

IV. Assay Device

In another aspect, the invention includes a device which can be used in accordance with the discussion in Section III above. The device includes (i) an absorbent pad for collecting oral fluid when placed in a subject's mouth, and (ii) reagent means for producing a threshold level of a colored reaction product when oral fluid from the pad is contacted with the reagent means for a selected time period, to indicate that an effective volume of undiluted saliva sample sufficient to allow detection of the analyte has been collected.

In one embodiment of the device, the reagent means includes a selected volume of solution of a chromogenic amylase substrate in a vial in accordance with the preceding section. Submersion of the adsorbent pad, after collection of oral fluid in the pad, in the solution for a selected time is effective to produce a threshold solution color when the pad contains an effective volume of undiluted saliva.

In another embodiment, the reagent means includes a chromogenic amylase substrate localized in a reaction region downstream (with respect to the direction of sample flow) from the absorbent pad, for receiving oral fluid collected in the pad. The reaction region may reside in a portion of the pad or in an appendage that is attached to the pad. The device also may include a detection region located downstream from the reaction region on the device, where the reaction and detection regions are spaced apart such that migration of oral fluid from the reaction region to the detection region occurs over the selected time period.

The device is configured such that after the selected reaction time period, the reaction region can be inspected to determine the level of such colored product produced. Production of a level of colored product above a selected threshold level indicates that an effective volume of undiluted saliva sample has been collected, sufficient to allow detection of the analyte of interest.

Figure 4:
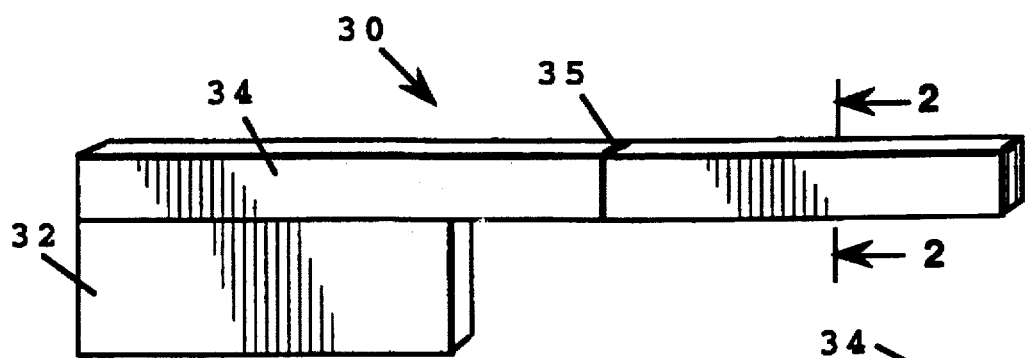
FIG. 4 shows a side view of another collection device in accordance with the invention.
Figure 5:
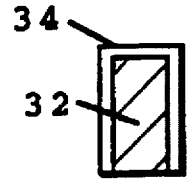
FIG. 5 shows a cross-sectional view of one end of the FIG. 4 device.

FIG. 4 shows an exemplary device in accordance with the invention. The device 30 includes an absorbent pad 32 and a holder element 34 which provides a means of holding the pad without the user's hand coming into contact with the pad. The device may also include a score mark 35 which allows the end of the holder distal to the pad to be broken off easily. FIG. 5 shows a cross-sectional view of the distal end of the holder, showing how the holder 34 encloses pad 32.

Pad 32 may be composed of any of the absorbent materials described in section II above which are compatible with absorbing oral fluid and which have little or no tendency to bind salivary components. Holder 34 may be made of any durable, inert material that is able to maintain a rigid shape. Preferably, the holder is made of a plastic material (polystyrene or the like) that is transparent along its entire length, allowing visualization of the pad material within.

Figure 6A:
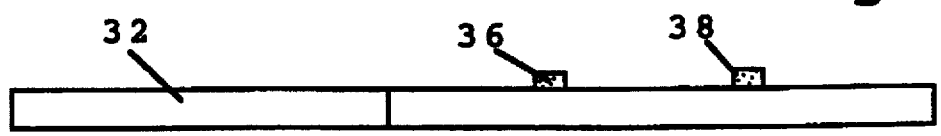
FIG. 6A and 6B show side and cross-sectional views of an absorbent pad in accordance with the invention.
Figure 6B:
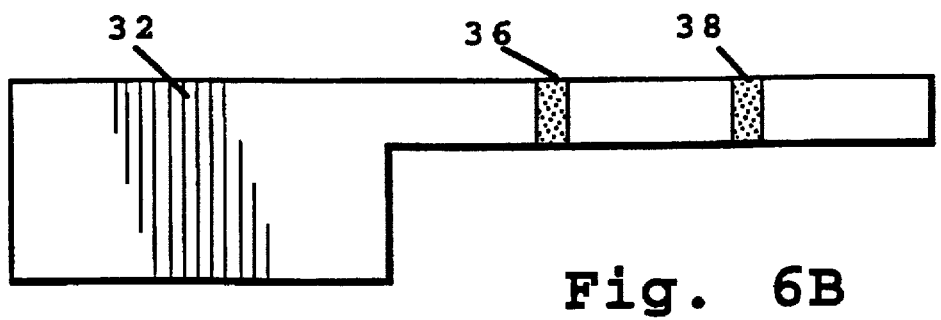

An exemplary pad in accordance with the invention is illustrated in FIGS. 6A and 6B. Pad 32 includes a main body portion (left side of FIG. 6A) which is joined to a handle portion (right side of figure) that extends away from the main body. The dimensions of the main body portion of the pad are typically chosen to hold a selected volume of saliva. For example, the amount of saliva to be absorbed in the pad may be between 0.4 and 1.0 mL, although other volumes may be satisfactory.

With continued reference to FIGS. 6A and 6B, the handle portion includes a reaction region 36 and a detection region 38. In the embodiment shown in FIG. 6B, regions 36 and 38 (shaded regions) are located on the surface of the pad. When the pad is combined with holder 34, regions 36 and 38 are enclosed by the holder (FIGS. 4 and 5).

Reaction region 36 contains the chromogenic substrate in dry form for reaction with the saliva sample. The reaction region may be prepared by applying an α-amylase substrate solution of the type described above over a narrow band in the handle region of the pad, and then allowing the solution to dry. Alternatively, particularly with reference to the embodiment in FIG. 6A, the α-amylase substrate may be applied to a separate piece of absorbent material which, after the substrate solution has dried, is then affixed to the main body of the absorbent pad.

The handle portion of the pad also contains a detection region 38 which is more distant from the main body of the pad than region 36; in other words, region 38 is downstream from region 36 with respect to the direction of flow of oral fluid in the pad. Region 38 contains an indicator substance which changes color or opacity when contacted with an aqueous solution such as saliva. The region may be prepared by application of a solution to the absorbent pad or to a separate material that is then joined to the pad in the same manner as for region 36 above.

Reaction region 36 and detection region 38 are spaced apart from each other so that the time for sample fluid to migrate from region 36 to region 38 is the same as the desired reaction time, e.g., 2 minutes.

Figure 7A:
FIGS. 7A and 7B illustrate operation of the FIG. 6 pad, showing the changes in color that occur in reagent bands located in the pad after contact with saliva.
Figure 7B:
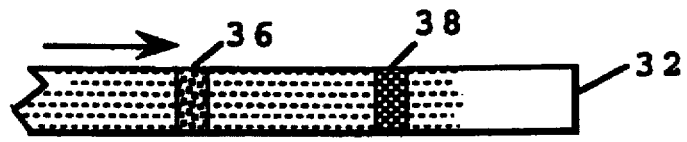

The roles of regions 36 and 38 will be better appreciated from FIGS. 7A and 7B. A saliva sample is collected from the subject's mouth using device 30 as shown in FIG. 4. After the main body of the pad has become substantially wetted, the device is withdrawn from the subject's mouth and placed in an empty vial. During this time, the sample fluid in the main body of the pad begins to migrate into the handle portion of the pad. Migration into reaction region 36 initiates amylase-catalyzed cleavage of the chromogenic substrate to produce colored product within the reaction region. It will be appreciated that localization of the substrate in a portion of the absorbent pad that is outside the main path of fluid flow (see region 36 in FIG. 6A) allows the bulk of the substrate and colored product that is produced to remain in region 36 during fluid flow.

After passing through region 36, the sample passes through detection region 38, causing a change of color or opacity due to hydration of the indicator substance. Suitable indicator substances include, for example, anhydrous copper (II) sulfate, which changes from colorless to blue upon hydration, and cobalt(II) chloride, which changes from blue to pink upon hydration. It will be appreciated that the device should be stored in a water-free environment, preferably in the presence of a desiccant, to prevent hydration of the water-sensitive indicator prior to use.

When hydration of detection region 38 is complete, reaction region 36 is inspected to determine whether the amount of colored product generated is greater than the selected threshold intensity, as judged by comparison with a suitable color swatch. A level of colored product greater than the threshold intensity indicates that the sample is sufficient to allow reliable detection of the analyte of interest. A level of product below the threshold indicates that the sample should not be relied on, particularly if the sample later tests negative for analyte, and that another sample should be collected.

It will be appreciated that the flow rate of the sample through the handle portion of the pad can be controlled by suitable choice of pad material and by the cross-sectional dimensions of the handle. Thus, these parameters, together with the spacing between reaction region 36 and detection region 38, can be used to achieve a desired migration time between regions 36 and 38 that is equal to the desired reaction time for the amylase reaction.

The device of the invention may also be employed in a kit for testing a human oral fluid sample for the presence of a selected analyte. The kit generally includes (i) an absorbent pad for collecting oral fluid when placed in a subject's mouth, and (ii) reagent means-for producing a threshold level of a colored reaction product when oral fluid obtained from the absorbent pad is contacted with the reagent means for a selected time period, to indicate that an effective volume of undiluted saliva sample sufficient to allow detection of the analyte in such assay has been collected.

The kit preferably includes one or more color swatches as intensity standards for determining whether the amylase level in the sample is consistent with sample sufficiency as set forth above.

The kit may also include an assay device for the analyte of interest (e.g., hCG), with the amylase detection means serving to determine whether a negative result can be relied upon.

V. Utility

The present invention provides an improvement in saliva-based analyte-detection assays for human subjects. Although detection of a selected analyte in a saliva sample is typically unequivocal in revealing the presence of a correlative disease state in the patient, a negative test result is less reliable since the result may reflect collection of an inadequately concentrated sample.

The present invention addresses this problem. By reacting the sample with a chromogenic substrate of salivary α-amylase and determining whether colored product above a preselected threshold level is produced, one can reliably determine whether the apparent absence of analyte reflects the true condition of the patient, e.g., that the patient does not have the disease being tested for.

In addition to providing such assurance, the invention provides a number of other important advantages. The method is simple to conduct, requiring only mixing or contacting the saliva sample with the chromogenic amylase substrate. The method allows the adequacy of the concentration and amount of sample to be determined within minutes so that the person collecting the sample can know right away whether another sample should be collected. Furthermore, by generating a colored product which can be easily visualized by the human eye, the method avoids the cost and added complexity of spectroscopic instrumentation.

Another advantage of the invention is that the α-amylase substrates, as exemplified by 2-chloro-4-nitrophenyl-α-D-maltotrioside, are stable in aqueous conditions. For example, a solution prepared according to the components and concentrations listed in Example 1 remained colorless for at least one year when stored in a sealed vial at room temperature. It is preferred that substrates having nitrophenol leaving groups also include additional electron-withdrawing groups on the phenol ring, since such substituents enhance the stability of the substrate in solution.

A further advantage of the α-amylase substrates employed by the invention is that the colored product does not interfere with subsequent detection of the selected analyte. Studies conducted in support of the invention have shown that the products from the reaction of α-amylase with the exemplary substrate 2-chloro-4-nitrophenyl-α-D-maltotrioside do not interfere with detection of a variety of analytes in saliva, including cotinine, cocaine, HIV-1-specific antibodies, and hepatitis B surface antigen, for example.

The following example(s) illustrate but are not intended in any way to limit the scope of the invention.

EXAMPLE 1

Amylase Assay Using Trisaccharide Substrate

In this study, a sample collection device available under the tradename "ORASURE" was used to collect saliva sample from 73 healthy subjects. The device consisted of a rectangular cotton pad having dimensions 3×1.25×0.15 cm connected to a 4 inch long plastic stick via a suitably sized groove in the handle. Prior to sample collection, the pads were saturated with a salt solution (3.5% sodium chloride, 0.3% citric acid, 0.1% potassium sorbate, 0.1% sodium benzoate, and 0.1% bovine gelatin, pH 7.2) and then dried.

Each subject placed an absorbent pad into his/her mouth (buccal space) for 2 minutes. The pad was then placed in a transparent polyethylene vial containing 0.8 ml of a substrate solution, and the development of a yellow color in the pad and solution was monitored. The substrate solution (which was colorless) contained the following components dissolved in water: 5 mM potassium phosphate, 5 mM sodium thiocyanate, "TWEEN-20" (0.5 wt. %), chlorhexidine digluconate (0.01 wt. %), and 0.76 mM 2-chloro-4-nitrophenyl-α-D-maltotrioside.

The intensity of the yellow color in each pad was monitored with respect to three color swatches having increasing intensities of yellow color (designated 1, 2, and 3), and the times when the color in the pads reached each intensity level was recorded. The results are shown in Table 1 above.

Although the invention has been described with respect to particular embodiments, it will be appreciated that various changes and modifications can be made without departing from the invention.

It is claimed:

1. A method of determining the adequacy of amylase concentration quality in saliva from an oral fluid sample for the purpose of ensuring reliable detection of an analyte other than amylase, said method comprising the steps of:
   i) collecting an oral fluid sample comprising amylase and suspected of containing the analyte;
   ii) detecting the amylase concentration in said sample; and,
   iii) comparing said amylase concentration to a standard concentration to determine if the sample comprises adequate amylase concentration quality to reliably detect the analyte.

2. The method of claim 1 wherein the analyte is an immunoglobulin.

3. The method of claim 1 wherein the analyte is an immunoglobulin specific for a pathogen selected from the group consisting of HIV-1, HIV-2, hepatitis B, measles, mumps and rubella.

4. The method of claim 1, wherein the analyte is selected from the group consisting of cocaine, benzoylegonine, cotinine, amphetamine, and methamphetamine.

5. A method of claim 1 wherein the concentration of amylase is determined by the step of contacting the sample with a chromogenic amylase substrate effective to produce a colored product upon reaction with/amylase.

6. A method of claim 5 wherein the substrate yields chloro-nitrophenol upon, contact with amylase.

7. A method of claim 5 which further comprises the steps of collecting the oral sample onto an absorbent pad and submerging the absorbent pad into a vessel having a known volume of reaction medium containing a chromogenie amylase substrate effective to produce a colored product upon reaction with amylase present in the sample.

8. A system for minimizing false negative results in an analyte detection assay for oral fluids where said negative results arise from dilution of the analyte due to excessive amounts of saliva, said system comprising:
   i) an apparatus having an absorbent means for collecting the oral sample comprising amylase and analyte by ensuring that the sample comprises an adequate amount of amylase;
   ii) a reagent for detecting amylase by producing a colored reaction product in the presence of amylase said reagent positioned in the system to permit contact between the oral sample the reagent; and,
   iii) a colored standard for determining relative amylase concentration in a position permitting comparison between the colored reaction product of step ii and the colored standard said standard at a predetermined color intensity to minimize false negative results in the oral sample due to inadequate analyte concentration where said inadequate analyte concentration is due to dilution from saliva.

9. A system of claim 8 wherein the means for collecting the oral sample is an absorbent pad.

10. The system of claim 8 wherein the analyte is an immunoglobulin.

11. The system of claim 8 wherein the analyte is an immunoglobulin specific for a pathogen selected from the group consisting of HIV-1, HIV-2, hepatitis B, measles, mumps and rubella.

12. The system of claim 8, wherein the analyte is selected from the group consisting of cocaine, benzoylegonine, cotinine, amphetamine, and methamphetamine.

13. A system of claim 8 where the means for collecting the oral sample and the reagent are positioned so that they are in fluid contact when the oral sample is present.

14. A system of claim 13 where the apparatus further comprises a detection region in fluid contact with the reagent said detection region detecting the physical volume of the oral fluid sample.

15. A system of claim 14 wherein the detection region is physically separated from the reagent.

16. An apparatus for minimizing false negative results in assays for detecting analytes in oral samples where the apparatus comprises:
   i) an absorbent means to collect an oral sample;
   ii) a chromogenie reagent in fluid contact with the absorbent means wherein the chromogenic reagent produces a colored product upon reaction with amylase; and,
   iii) a fluid detection region in fluid contact with the chromogenic reagent wherein the detection region permits visual detection of total fluid present in the apparatus and wherein the fluid detection region comprises a reagent that chromogenically responds to water in a manner that is not dependent upon the presence or absence of amylase.

17. The apparatus of claim 16 wherein the means for collecting the oral sample is an absorbent pad.

18. The apparatus of claim 16 wherein the detection region is physically separated from the, reagent.

19. The apparatus of claim 16 wherein the analyte is an immunoglobulin.

20. The system of claim 16 wherein the analyte is an immunoglobulin specific for a pathogen selected from the group consisting of HIV-1, HIV-2, hepatitis B, measles, mumps and rubella.

* * * * *